United States Patent [19]
Davis

[11] 3,954,108
[45] May 4, 1976

[54] OCCLUSION CLIP AND INSTRUMENT FOR APPLYING SAME

[76] Inventor: Hugh J. Davis, 2 E. Highfield Road, Baltimore, Md. 21218

[22] Filed: Aug. 27, 1974

[21] Appl. No.: 501,079

Related U.S. Application Data

[62] Division of Ser. No. 303,314, Nov. 3, 1972, Pat. No. 3,856,016.

[52] U.S. Cl. ............................................. 128/325
[51] Int. Cl.² ......................................... A61B 17/12
[58] Field of Search ............................ 128/321, 325

[56] References Cited
UNITED STATES PATENTS

| | | | |
|---|---|---|---|
| 2,890,519 | 6/1959 | Storz, Jr. | 128/325 X |
| 3,270,745 | 9/1966 | Wood | 128/325 |
| 3,326,216 | 6/1967 | Wood | 128/325 |
| 3,378,010 | 4/1968 | Codling | 128/325 |
| 3,463,156 | 8/1969 | McDermott | 128/325 |
| 3,518,993 | 7/1970 | Blake | 128/321 |
| 3,777,538 | 12/1973 | Weatherly et al. | 128/325 |
| 3,814,102 | 6/1974 | Thal | 128/321 |
| 3,827,438 | 8/1974 | Kees, Jr. | 128/325 |

*Primary Examiner*—Channing L. Pace

[57] ABSTRACT

An instrument is provided for applying an occlusion clip on an anatomical tubular structure such as a fallopian tube. An elongated housing can be inserted through a narrow incision, and carries at its forward end a pair of jaw means for applying a clip which is composed of a bendable material. The jaw means are movable relative to one another with the bendable clip disposed between them. Longitudinally reciprocable actuating means extends along the length of the elongated housing, so that the jaw means may be operated from the rearward end of the elongated housing. The jaw means have forward ends which are movable toward and away from each other to close and to open the jaws, and the jaw means have rearward ends which are always spaced apart from each other throughout the closing and opening movement of the jaws, to provide controlled pressure on the tubular member without completely crushing it.

9 Claims, 16 Drawing Figures

OCCLUSION CLIP AND INSTRUMENT FOR APPLYING SAME

This application is a division of copending application Ser. No. 303,314, now U.S. Pat. No. 13,856,016, dated Dec. 24, 1974.

The present invention relates to an instrument to apply an occlusion clip.

Various clips are known in the prior art for causing an occlusion of anatomical tubular structures such as blood vessels, veins, etc. A clip designated "Hemoclip" is known in the art which consists of a thin wire bent into approximately U-shape. While this Hemoclip has been used with some success, certain problems nevertheless exist with this prior art type of occlusion clip because, if the wire is applied too tightly, it will cut into the tubular structure. Furthermore, if the wire of this prior art clip is too narrow, as is the case, then the specific pressure becomes excessively high. Since a certain width is necessary to assure a satisfactory occlusion, it is customary to apply two or three of these so-called "Hemoclips" to a given anatomical tubular structure. Additionally, these prior art occlusion clips are susceptible, by reason of their construction, of slipping off from the anatomical tubular structure while being applied or even thereafter, i.e., there is always the danger that these prior art clips do not stay in the desired position, thereby resulting in eventual failure of the occlusion.

An instrument called "Laparoscope" is known in the art for purposes of sterilization by cauterizing fallopian tubes. After causing ballooning of the abdominal wall, a narrow slit is made through the umbilicus to thereafter insert the Laparoscope, and with the assist of fiber-optics, cauterization is effected. However, this method of sterilization is fraught with certain dangers as some difficulties exist in controlling the degree and extent of cauterization in order to avoid accidental burning of adjacent parts, such as intestinal portions.

The present invention is concerned with the task of providing an occlusion clip which includes means to lock the clip in position during its application so that the clip cannot come off the instrument used for applying the same.

The instrument in accordance with the present invention is provided with relatively movable jaws at the free end of a tubular member adapted to be inserted through an opening, for example, through the umbilicus whereby the jaws are provided with means to lock the occlusion clip in position while being inserted into the opening formed in the human body for eventual emplacement over the fallopian tubes or the like. By providing one of the jaws with a projecting nose portion and the occlusion clip with a complementary slot, the occlusion clip in accordance with the present invention is securely held in position until actually installed over the anatomical tubular structure.

An advantage of the instrument in accordance with the present invention resides in the particular location of the fulcrum for the movable jaw to assure a closing of the free end of the lower jaw first, thereby assuring an occlusion without cutting into any tissues.

Another feature of the present invention resides in the simplicity of the instrument used for applying the occlusion clip which has a convenient pistol grip and permits a good view through its tubular member even when the jaws are closed, thus enabling accurate control in the positioning and application of the occlusion clip.

Accordingly, it is an object of the present invention to provide an occlusion clip and instrument for applying the same which avoid by simple means the aforementioned shortcomings and drawbacks encountered in the prior art.

It is another object of the present invention to provide an occlusion clip and instrument for applying the same which substantially eliminate failures in the occlusion due to faulty application.

A further object of the present invention resides in an instrument for applying an occlusion clip same which will provide occlusion at spaced points to minimize the likelihood of eventual failure of the occlusion.

Still another object of the present invention resides in an apparatus for applying an occlusion clip of the type described above which permits permeation likely to encourage fibrosis to assure a permanent interruption in the anatomical tubular structure.

Still a further object of the present invention resides in a combined occlusion clip and instrument for applying the same which assure reliable locking of the clip onto the instrument during the operation.

Another object of the present invention resides in an instrument for applying the occlusion clip of the present invention which is simple in construction, reliable in operation and permits easy handling by the availability of an optical viewing system enabling the doctor to visually follow the positioning and application of the clip throughout the entire operation.

These and further objects, features and advantages of the present invention will become more apparent from the following description when taken in connection with the accompanying drawing which shows, for purposes of illustration only, several embodiments in accordance with the present invention, and wherein.

Figure 2:
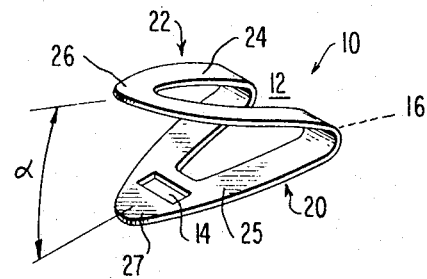
FIG. 2 is a perspective view of a clip formed from the blank of FIG. 1 by bending the blank back upon itself into a configuration ready for insertion into the open jaws of the instrument.
Figure 3:
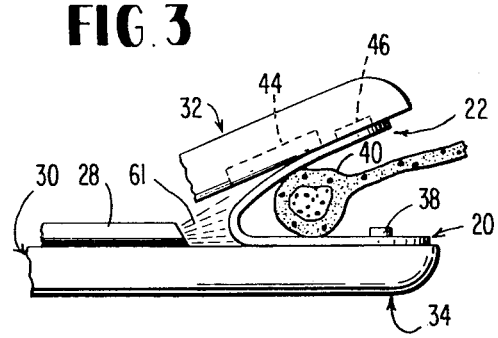
Figure 4:
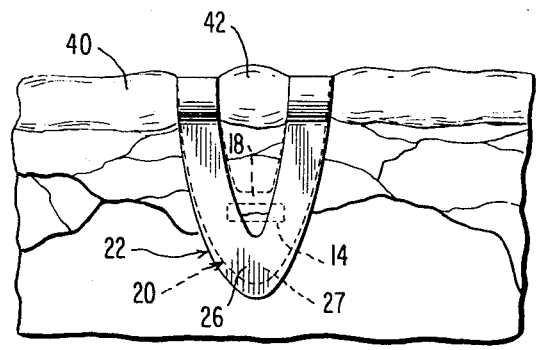
Figures 5, 8:
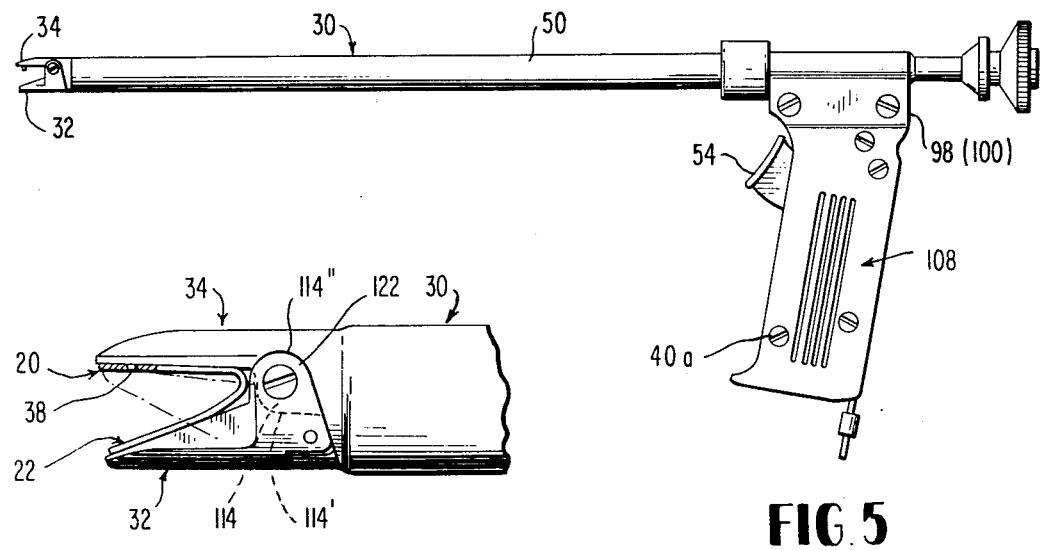
Figure 6:
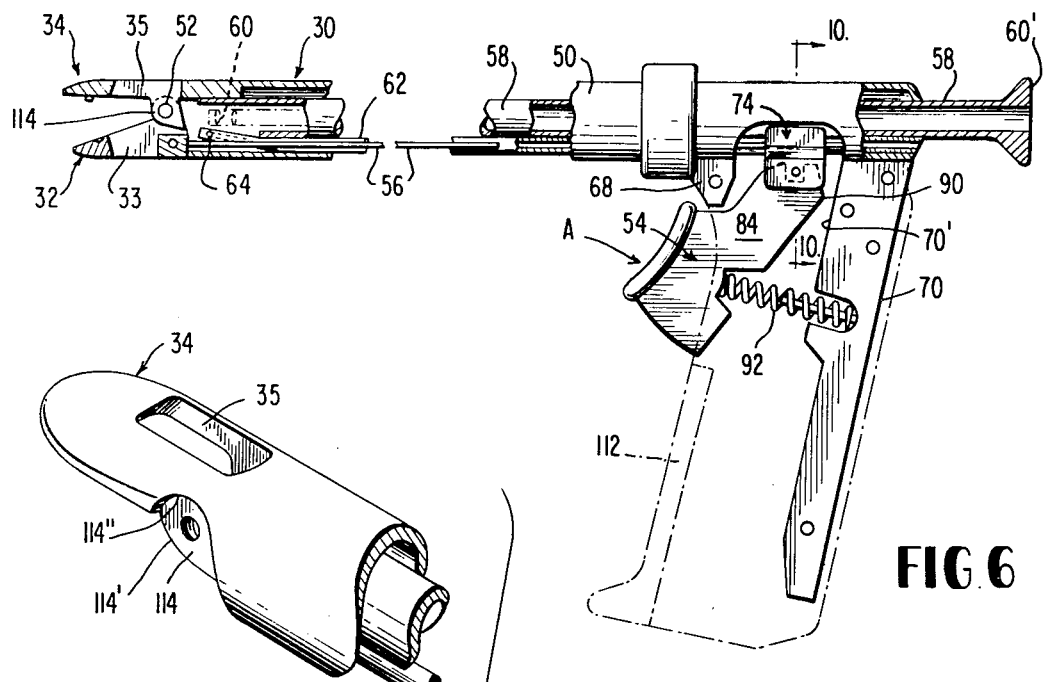
Figure 7:
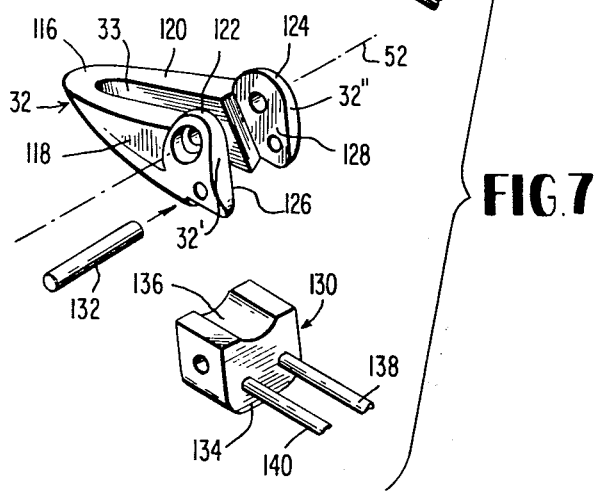
Figure 10:
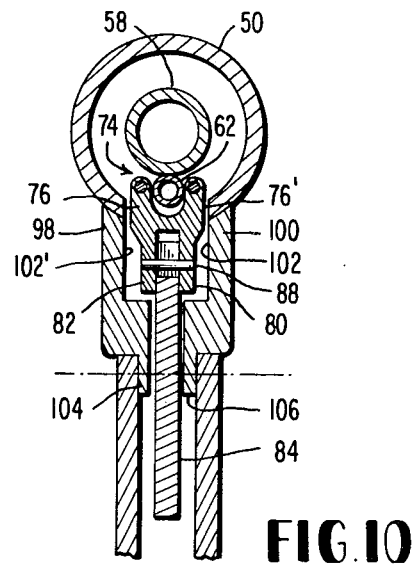
Figure 11:
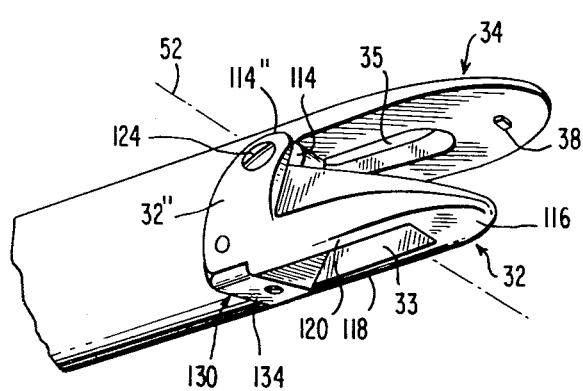
Figure 15A:
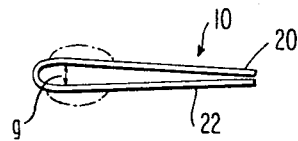
Figure 15B:
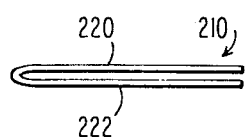
Figure 12:
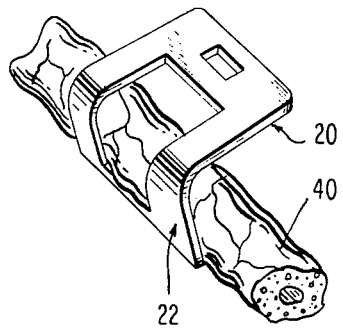
Figure 9:
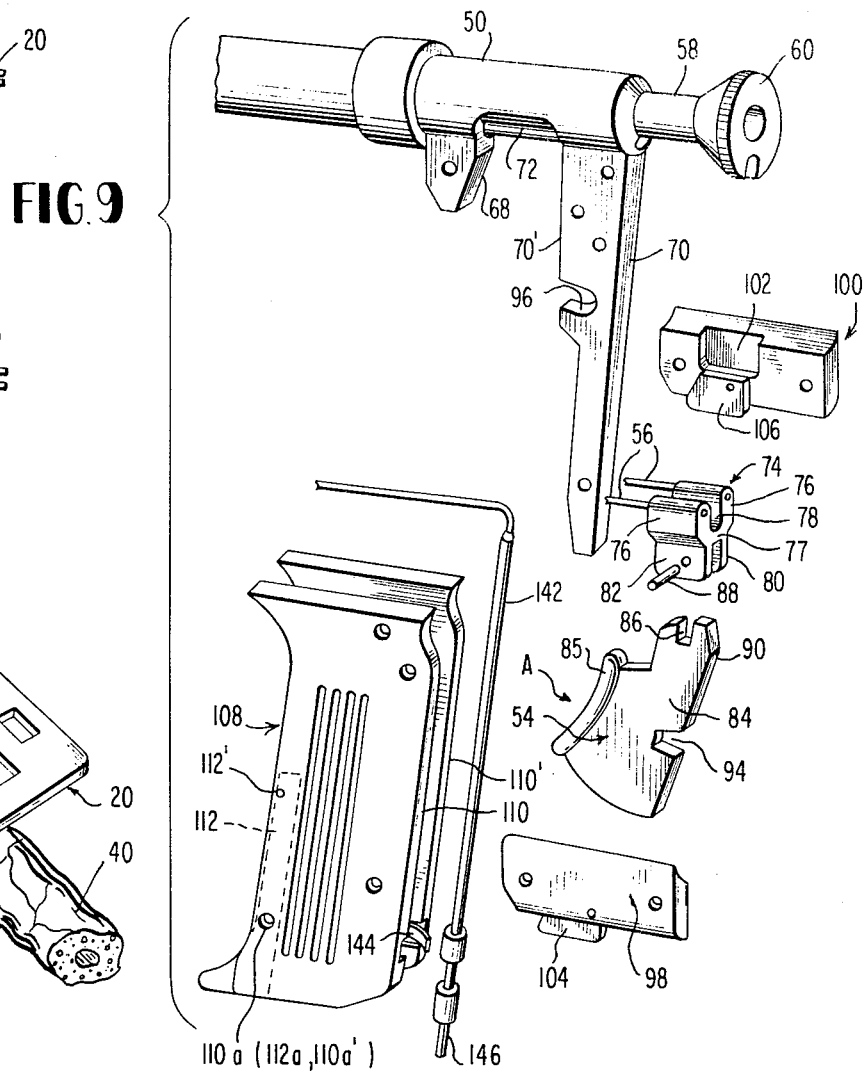
Figure 13:
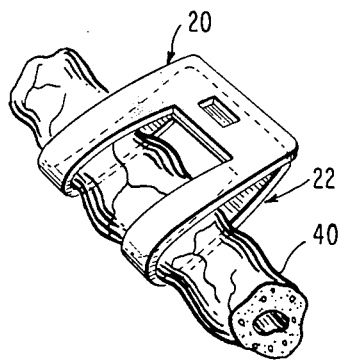
Figure 14:
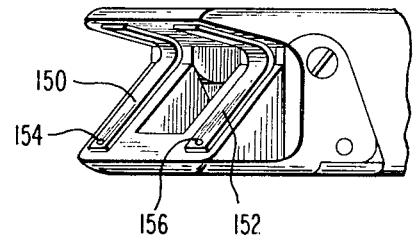

FIG. 3; is a somewhat schematic side view illustrating the application of the occlusion clip shown in FIG. 2 on an anatomical tubular structure;

FIG. 4 is a fragmentary view showing the occlusion clip clamped on the anatomical tubular structure of FIG. 3;

FIG. 3 is a side view of an instrument in accordance with the present invention for applying the occlusion clip of FIG. 2 on the anatomical tubular structure;

FIG. 6 is a fragmentary view, partially in longitudinal cross section, through certain parts of the instrument of FIG. 5;

FIG. 7 is an exploded perspective view of the front part of the instrument of FIGS. 5 and 6;

FIG. 8 is an enlarged side view of the front part of the instrument of FIG. 5 illustrating the jaw portions thereof;

FIG. 9 is a perspective, exploded view of the rear part of the instrument shown in FIG. 5;

FIG. 10 is a cross-sectional view, on an enlarged scale, through the instrument of the present invention taken along line X—X of FIG. 6;

FIG. 11 is a perspective view, on an enlarged scale, of the front part of the instrument in accordance with the present invention;

FIG. 12 is a perspective view of the occlusion clip in relation to the anatomical tubular structure at the beginning of its application;

FIG. 13 is a perspective view, similar to FIG. 12 and showing the relationship of the occlusion clip to the anatomical tubular structure as the application proceeds;

FIG. 14 is a perspective view of the front part of a modified embodiment of an instrument in accordance with the present invention; and FIGS. 15a and 15b are schematic side views comparing the installed clip of the present invention with the installed clip of the prior art, respectively.

Figure 1:
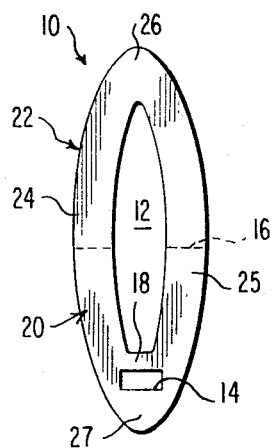
FIG. 1 is a plan view of an occlusion clip blank in accordance with the present invention.

Referring now to the drawing wherein like reference numerals are used throughout the various views to designate like parts, the occlusion clip blank generally designated by reference numeral 10 is in the form of a unitary structure which includes two lateral portions 24 and 25, constituting in effect two occlusion clip members spatially separated from one another, a connecting portion 26 at the upper end, as viewed in FIG. 1 which connects the side portions 24 and 25 and a connecting portion 27 connecting the side portions 24 and 25 at the lower end. An indexing aperture 14 is also provided in the lower connecting portion 27 which is intended to engage with an indexing projection 38 (FIGS. 3, 8, and 11) provided on the fixed jaw 34 of the instrument of this invention for positioning the occlusion clip 10 in relation to the instrument and to thereby lock the same in position.

It will be appreciated that the occlusion clip of FIGS. 1 and 2 provides in effect for an elongated opening or hiatus 12 defining a herniating divider portion 18 thereby separates this hiatus 12 from the indexing aperture 14.

For purposes of use with the instrument in accordance with the present invention, the occlusion clip blank 10 made of suitable flexible material is bent back upon itself about the flex line 16 to provide two half portions generally designated by reference numerals 20 and 22 such as illustrated in FIG. 2. The blank 10 should thereby be bent only to such an extent that the two portions 20 and 22 subtend therebetween an angle slightly larger than the angle of the two jaws 32 and 34 when in the fully opened position as shown in FIG. 3 so that the occlusion clip will securely lock in place by engagement of its aperture 14 with the nose-like indexing projection 38.

It may also be appropriate to impart a curved configuration to the portion 22 when bending the blank 10 back upon itself as shown in FIG. 3. Additionally, it may also be convenient to permit the portion 22 to be slightly longer than the portion 20, for example, by an amount of about 1/24 to 1/32 inch.

Of course, in lieu of the approximately oval shape of the blank 10 it is also possible to make the blank 10 of any other configuration, for example, of substantially rectangular configuration, in which case the occlusion clip portions 24 and 25 would be parallel to one another while the end portions 26 and 27 as well as the separating portion 18 would be at right angle thereto.

Referring now to FIGS. 5–11, the instrument for applying the occlusion clip according to this invention is in the form of an elongated tubular structure generally designated by reference numeral 30 (FIG. 5) which is provided at the left end thereof as viewed in FIG. 5 with jaws 32 and 34. In the illustrated embodiment, the jaw 34 is formed as an integral part of the tubular member 50 adjacent the left end thereof as viewed in FIG. 5. On the other hand, the jaw 32 is pivotal about an axis 52 (FIGS. 7 and 11) between its open, clip receiving position (shown in full line in FIG. 8) and the clip-applying position shown in dash line in FIG. 8. Due to the slight eccentricity of the pivot axis 52, the closing movement of the jaw 32 is such that the free end of the jaws 34 and 32 will come into abutment against one another while also forming a narrow tapering space increasing in the direction toward the gripping portion generally designated by reference numeral 108. This particular closing movement assures that the free ends constituted by the connecting portions 26 and 27 are closed before the entire occlusion clip is more or less flattened out, thereby preventing a slipping off of the occlusion clip from the anatomical tubular structure such as a fallopian tube, when being applied and assuring other advantages as will be described more fully hereinafter by reference to FIGS. 15a and 15b.

On the side of the tubular member 50, opposite the jaws 34 and 32, i.e., on the right side as viewed in FIG. 5 is provided the handle generally designated by reference numeral 108 which includes an actuating member 54 in the form of a trigger, connected with the movable jaw 32 by way of the control linkage as will be described more fully hereinafter.

A separate tube 58 (FIG. 6) is provided on the inside of the tubular structure 50 for receiving and positioning an optical device of conventional construction, the front end of which is schematically indicated and designated in FIG. 6 by reference numeral 60. At its opposite end, the tube 58 is provided with a conventional eye piece 60' which may be adustable if so desired. The viewing means 58, 60 and 60' permits the user of the instrument to view between the opened jaws as well as between the separated clamping portions 24 and 25 of the occlusion clip when in the initial position during the application as shown in FIG. 3, thus permitting a continuous viewing of the insertion of the instrument through the opening in the umbilicus and during the positioning thereof over the fallopian tube. The instrument also includes further means to produce a light beam 61 (FIG. 3) to illuminate the area between the jaws and in front thereof so as to facilitate the proper positioning and application of the occlusion clip over the anatomical tubular structures, especially the fallopian tube. These illuminating means may be of any conventional type, for example, in the form of another tube 62 which extends through the tube 50 and includes a light source, for instance in the form of a small lamp designated in FIG. 6 by reference illumination to facilitate the positioning and application of the occlusion clip. However, in lieu of utilizing a light source 64 located at the end of the tube 62, it is preferable to use a light source in the form of conventional fiber-optics and constituted by the tube 62 with the primary light source for the fiber-optics located internally or preferably externally at any appropriate place on the instrument. Since such fiber-optical illuminating devices are known as such, a detailed description thereof is dispensed with herein.

As shown in FIG. 9, a pair of support projections 68 and 70 for the handle structure are secured to the tube 50 by conventional means. These supporting projections 68 and 70 are thereby located on both sides of an elongated recess 72 in the tube 50. The recess 72 slidably receives a slidable control member generally designated by reference numeral 74 and enables reciprocation thereof in the axial direction of the tube 50 between the two supporting projections 68 and 70. The slidable control member 74 includes a U-shaped upper body part formed by leg portions 76 and 76' connected by web portion 77 in such a manner that a substantially U-shaped recess 78 is formed. This recess 78 is so shaped as to receive the tubular member 62 for the illuminating device so that the slidable control member 74 is guided in its to and fro movement on the tube 62 when the control member is assembled in its position as shown in FIGS. 6 and 10. Additionally, the slidable control member 74 includes a pair of depending leg portions 80 and 82 spaced from one another to receive the body portion 84 of the trigger member 54. The body portion 84 is provided with a rectangular notch 86 to receive a pin 88 which extends across the U-shaped channel between the projecting leg portions 80 and 82. When the trigger member 54 is installed so that the pin 88 comes to lie in slot 86, the slidable control member 74 and trigger member 54 are in effect pivotally connected with each other. The trigger plate 84 is further provided with a corner 90 which, as shown in FIG. 6, is adapted to engage with the surface 70' of the supporting projection 70 so that in case of application of a force in the direction of arrow A (FIGS. 6 and 9), the corner 90 will abut at the surface 70' and thus constitutes a fulcrum about which the trigger member 54 will rotate in the counterclockwise direction, thereby imparting a sliding movement to the slidable control member 74 toward the left direction, as viewed in FIG. 6, which is made possible by the pivotal connection 86, 88, between these two parts. Thus, the camming action between corner 90 and surface 70' translates the force A into sliding movements of the slidable control member 74.

A return spring 92 is interposed between the trigger plate 84 and the relatively stationary support member 70 and engages at its left end in a recess 94 provided in the trigger plate 84 and at the right end in the recess 96 provided in the supporting member 70.

The handle structure 108 further includes a pair of cover plates 98 and 100 (FIGS. 9 and 10), each provided with a recess 102 and 102', recess 102 being shown clearly in FIG. 9. The recesses 102 and 102' are intended to receive the leg portions 80 and 82 of the sidable control member 174. Additionally, the cover members 98 and 100 are provided with depending plate-like leg portions 104 and 106 which act as guide means for the trigger plate 84 when the parts are in the assembled position thereof as shown in FIG. 10. The handle assembly further includes a cover structure generally designated by reference numeral 108 which has a pair of parallel-spaced cover plate portions 110 and 110' connected by means of a rib 112 (FIG. 6). The cover plates 98 and 100 and the cover plate portions 110 and 110' as well as the rib 112 of the cover structure 108 are secured to the support members 68 and 70 by means, for example, of screws which extend through screw holes as indicated. However, any other suitable fastening means may also be used to hold the parts in their assembled position. The rib 112 is also held fast in its proper position by the two-point connection constituted by the pin-type pivotal connection 112' and the screw extending through aligned holes 110a and 112a and the hole 110a' (not shown) in the cover portion 110'.

As shown in particular in FIGS. 7, 8 and 11, the jaw 34 is formed as an integral part of the exterior tube 50 adjacent its left end as viewed in FIGS. 5 and 6, and includes inwardly thereof lug portions 114 for pivotally supporting thereon by means of screws or the like the movable jaw 32. The lug portions 114 which are of approximately partially circular shape, provide guide surfaces 114' for the pivotal movement of the movable jaw member 32 which is also guided along the guide surfaces 114'' (FIGS. 8) constituted by the cut-out portions provided in the fixed jaw 34 to accommodate the side members 32' and 32'' of the movable jaw 32. As shown particularly in FIG. 11, the fixed jaw 34, in addition to the nose-like indexing projection 38 is also provided with an aperture 35.

The movable jaw 32 includes a transverse end portion 116 and spaced side portions 118 and 120 each provided with bearing portions 122 and 124 at the side members 32' and 32'' thereof and adapted to engage with the stationary bearing surfaces 114''. The jaw 32 is thereby pivotally supported on the lug portions 114 by any suitable means such as screws. Below the bearing surfaces 122 and 124 the leg portions 32' and 32'' are provided with opposite aligning recesses 126 and 128 to receive a reciprocal, slidable control member generally designated by reference numeral 130 which is pivotally connected with the side members 32' and 32'' by means of a pivot pin 132. The slidable control member 130 has an exterior configuration 134 at the bottom thereof to permit substantial alignment with and sliding movement along the inner surface of the outer tube 50. Additionally, the slidable control member 130 has an interior cylindrical recess 136 to provide for a substantially cylindrical aperture adjacent the jaw end of the tubular structure 50.

The slidable control member 130 is connected with the slidable control member 74 by means of a pair of elongated members 56 such as steel wires which are sufficiently stiff and rigid to cause the sliding control member 130 to partake in the reciprocation of the sliding control member 74 in response to actuation of the trigger 54.

In the illustrated embodiment, the illuminating device is in the form of an elongated tubular cable protective structure 62 for conducting by means of a cable disposed therewithin the supply voltage to a small electric bulb arranged at the front end thereof and indicated schematically by reference numeral 64 in FIG. 6. Appropriately the rear end of the cable protective structure or of the cable itself which extends through the tube 62, is bent downwardly as shown at 142 in FIG. 9 to be received between the side plates 110 and 112 so as to be protected thereby and held in position by means of a leaf spring 144 or the like. A power supply such as a battery can be connected to the lower end at 146 (FIG. 9).

However, as mentioned above, in lieu of the electrical connection extending through the tube 62, and the bulb 64, conventional fiber-optical means are preferably used to produce the desired illumination. The light source in the form of a suitable small incandescent high power lamp or the like may then be located in any suitable place, for example, externally of the tubular member 50, e.g., at the end of the portion 142, thereby obviating the need for the electrical cable and the bulb and the problem of replacing the same if wear occurs.

The optical device to be used with the instrument of the present invention, is in the form of an elongated structure and includes a number of optical lenses of conventional type as know in the art. Since the optical device, except for its particular location and association with the instrument of the present invention forms no part thereof, a detailed description is dispensed with herein.

As will be understood from the foregoing description of the instrument and occlusion clip of the present invention, the clip may be applied under direct continuous vision through the optical system during the operation. To that end, the movable jaw 32 is also provided with an aperture 33 so that continued viewing is made possible even after the free end of the movable jaw 32 abuts at the free end of the fixed jaw 34.

In actual use, the occlusion clip is positioned between the jaws as shown in FIG. 3 with the indexing projection 38 engaging in the indexing aperture 14 of the occlusion clip. After the introduction of the instrument through the umbilicus, it is properly positioned over the fallopian tube or the like, and with the aid of the illumination and the optical device, the location of the fallopian tube or other anatomical tubular structure becomes an easy matter for a trained surgeon. Since the fallopian tube can be observed directly through the opening 12 of the occlusion clip, i.e., through the spacing between the lateral clip portions 24 and 25, it is also easy to properly approach the anatomical tubular structure as well as to ascertain when the clip is in proper position relative thereto as shown in FIG. 12. In this position, the trigger 54 is actuated and the occlusion clip is closed on the tube 40 as shown in FIG. 13.

As can be seen from FIGS. 6, 8 and 11, the pivot point of the movable jaw 32 is slightly eccentric. This eccentricity in combination with the configuration of the portion 22 of the occlusion clip which, as mentioned hereinabove may be slightly curved, provides for a safe closing of the clip on the tube without crushing the tube to an extent that might otherwise cause damage or slipping off. This is a very important feature since the particular angulation of the jaws 32 and 34 and/or the height of the indexing tooth 38 permit that the separation of the occlusion clip arms, in the applied position, can be precisely predetermined. This is illustrated in FIGS. 15a and 15b, illustrating respectively somewhat schematic side elevational views of a clip in accordance with the present invention and of a clip of the prior art type, both when in the applied condition. In the clip 10 according to the present invention a predetermined separation or gap $g$ exists between the two arm portions 20 and 22, when applied, within the area receiving the anatomical structure. This separation $g$, which can be precisely predetermined by the design of the instrument of this invention, i.e., by the eccentricity of the pivot point of the movable jaw 32 and/or the height of the indexing tooth 38, may be about 0.8 mm which has been determined optimum for certain applications, and can be varied in a simple manner, if necessary, to a value greater or smaller than 0.8 mm, for example, to 0.5 mm if the thickness of the anatomical structure or of its tissue walls so demands. This is very important because if a clip is closed fully flat, as is the case in the prior art, illustrated in FIG. 15b where similar reference numerals of the 200-series are applied to similar parts, the tissue is crushed, thereby becomes avascular, necroses and cuts through, resulting in fistule formation and failures. In contrast to the present invention the prior art offers no means of controlling the closure by simple means and therewith offers no means effectively avoiding such failures.

It should also be mentioned that the opening 12 in the clip 10 performs the important function in the applied condition. On the one hand it acts as a pressure relief means and on the other, assists in locking the clip in position on the anatomical structure. The openings 33 and 35 in jaws 32 and 34 perform similar functions during the application. These two functions are only schematically indicated in dash and dot lines in FIG. 15a, showing the possibility of parts of the tissues of the anatomical structures to pass through opening 12.

While the mutually facing surfaces of the two jaws 32 and 34 are flat and parallel to one another, it may also be advantageous to use a different arrangement. For example, the surfaces need not be parallel to one another but may form a slight angle therebetween by appropriate beveling of one or both jaws in such a manner that the separation $g$ is, for example, about 0.8 mm on one side of the clip and say 0.5 mm, on the other side. Furthermore, the surfaces need not necessarily be flat for this purpose. However, it is quite apparent that the "controlled closure" is still present in the non-parallel arrangement of the jaw surfaces, resulting in the avoidance of the failures of the prior art.

It will thus also be appreciated that slippage of the anatomical tubular structure during the clamping operation is prevented because of the herniation of the tissue during the earliest phase of closure and the particular closing movement of the jaws causing a near closing at the free ends of the jaw members 32 and 34 before final closing of the occlusion clip.

Though the occlusion clip of FIG. 1 is particularly desirable because of its two spaced clip portions 24 and 25, other types of occlusion clips having spaced clip members may be employed within the scope of this invention. A possible modification is shown in FIG. 14 which shows the front end of the instrument with an occlusion clip in the form of two completely separate narrow clip members 150 and 152 positioned relative to the jaws by means of individual indexing means 154 and 156. This will permit the application of entirely separate clips in one and the same operation.

Additionally, it is also possible within the scope of this invention to modify the occlusion clip shown in FIGS. 1 and 2 by leaving out the connecting portion 26 or 27 and/or the divider 18. In that case, an indexing means in one of the jaws may be in the form of a rib which extends transversely to the jaw adjacent the edge thereof operable to engage the edge of the connecting portion 26 left between the side members 24 and 25.

Furthermore, it is also possible to construct the instrument with jaws extending substantially perpendicular to the longitudinal axis of the tubular structure 50. In that case, it will only be necessary to include a prism or the like in the optical system to conduct the light rays around the then existing corner.

While the present invention finds particular application for purposes of sterilization in connection with the fallopian tubes, its application is not limited thereto. For example, in smaller versions, the present invention can also be used for ligations, for example, blood vessels or the like. In that case, the present invention still entails the advantage of requiring only a single application in lieu of the need for a repeated application of two or more clips.

Furthermore, though the use of the instrument through the umbilicus has been described, its use is not limited thereto but could be used equally successfully for sterilization after the delivery when the fallopian tubes can be made accessible by merely a small incision due to the enlarged condition of the uterus. Furthermore, in addition to the direct application to the fallopian tubes, the instrument may be used also for purposes of ligation of vas deferens in males. In all of these and other "cover" uses of the clip, the instrument can be simplified by omitting its optical system and/or its light source, thus resulting in a less costly instrument, still entailing the same advantage of "controlled closure" of the clip. Furthermore, the instrument is not limited to the particular actuating mechanism as shown and described but any other actuating mechanism may be equally used which converts the actuating movement into pivotal movement of the movable jaw. For example, in an instrument without optical system and light source, the tubular structure 50 can be omitted and the means for actuating the movable jaw can then be greatly modified and simplified in a conventional manner, substituting another type of actuating mechanism for the one illustrated herein.

Finally, the present invention is equally applicable under culdoscopy for application through a culdoscope or similar device.

Any suitable material having the requisite physical properties may be used for the occlusion clip in accordance with the present invention, tantalum being among the preferred materials.

While I have shown and described several embodiments in accordance with the present invention, it is understood that the same is not limited thereto but is susceptible of numerous changes and modifications as known to those skilled in the art, and I therefore do not wish to be limited to the details shown and described herein, but intend to cover all such changes and modifications as are encompassed by the scope of the appended claims.

What I claim is:

1. An instrument for applying an occlusion clip on an anatomical tubular structure, which clip is composed of a bendable material, comprising an elongated substantially tubular housing of at least sufficient length to extend through an opening in the umbilicus to a position adjacent the fallopian tube, said tubular housing carrying at its forward end a pair of jaw means which are movable relative to one another with the bendable clip disposed between said jaw means between an open, clip-receiving position and a closed, clip-applying position, said jaw means extending longitudinally beyond the forward end of said substantially tubular housing but having a width when said jaw means are in an open position that is compatible with the width of said housing, for insertion while said jaw means are in an open position, into an incision of such small size as to accommodate said housing, actuating means on said instrument and reciprocable longitudinally of said housing for selectively closing the jaw means including control means for producing a controlled closure of the clip from said open, clip-receiving position to said closed, clip-applying position, said jaw means having forward ends which are movable toward and away from each other to close and to open said jaws, and said jaw means having rearward ends which are spaced apart from each other, throughout the closing and opening movement of said jaws.

2. An instrument according to claim 1, characterized in that one of said jaw means is pivotal relative to the other jaw means, and the tip ends of said jaw means are closer to each other than the rearward portions of said jaw means, and in that said control means produces pivotal movement of said pivotal jaw means relative to the other jaw means in such a manner that the free end thereof nears abutment with the free end of the other jaw means before any other portions of the jaw means come into mutual engagement.

3. An instrument according to claim 2, characterized in that one of the jaw means includes securing means for engagement with a complementary securing means on the occlusion clip to be installed between the jaw means.

4. An instrument according to claim 3, characterized in that the securing means at one of said jaw means is in the form of a projection carried by said jaw means and the complementary securing means is in the form of an aperture formed in the occlusion clip complementary to said projection.

5. An instrument according to claim 2, characterized in that said pivot is positioned longitudinally off center, and that said actuating means includes a handle portion together with longitudinally reciprocable means for opening and closing said jaw means.

6. An instrument according to claim 1, characterized in that the jaw means are provided with substantially flat surfaces facing one another and forming an angle in the open, clip-receiving position which is substantially less than 90°.

7. An instrument according to claim 1, characterized in that the jaw means are provided with non-parallel flat surfaces facing one another.

8. An instrument according to claim 1, characterized by provision of a securing means in the form of a male member projecting from one of said jaw means for engaging into a complementary aperture provided in the occlusion clip.

9. An instrument according to claim 8, characterized in that at least one jaw means is provided with a pressure-relief aperture means adjacent its forward end and arranged in position to receive said securing means which projects from the other jaw, when said jaw means approach their closed position.

* * * * *